US007827039B2

(12) United States Patent
Butcher et al.

(10) Patent No.: US 7,827,039 B2
(45) Date of Patent: Nov. 2, 2010

(54) PERSONALIZED AUDIO/VIDEO/TEXT WELLNESS PROGRAM

(76) Inventors: Jon David Butcher, 37W766 Woodgate Rd., St. Charles, IL (US) 60175; Patrick Gentempo, Jr., 1 International Blvd., Mahwah, NJ (US) 07495

(*) Notice: Subject to any disclaimer, the term of this patent is extended or adjusted under 35 U.S.C. 154(b) by 1063 days.

(21) Appl. No.: 10/594,786

(22) PCT Filed: Apr. 1, 2005

(86) PCT No.: PCT/US2005/011034
§ 371 (c)(1),
(2), (4) Date: Sep. 29, 2006

(87) PCT Pub. No.: WO2005/098715
PCT Pub. Date: Oct. 20, 2005

(65) Prior Publication Data
US 2009/0055214 A1 Feb. 26, 2009

Related U.S. Application Data

(60) Provisional application No. 60/559,253, filed on Apr. 1, 2004.

(51) Int. Cl.
*G06Q 50/00* (2006.01)
(52) U.S. Cl. .......................................................... 705/2
(58) Field of Classification Search ...................... 705/2
See application file for complete search history.

(56) References Cited

U.S. PATENT DOCUMENTS 5,692,501 A * 12/1997 Minturn ...................... 600/301
6,039,688 A * 3/2000 Douglas et al. .............. 600/300
2003/0204412 A1* 10/2003 Brier .............................. 705/2
2004/0267565 A1* 12/2004 Grube ........................... 705/2
2005/0228692 A1* 10/2005 Hodgdon ....................... 705/2

OTHER PUBLICATIONS

PR Newswire, "Starting Today, AccentHealth, Inc. Offers a Deep and Intuitive New Health and Wellness Information Web Site Designed to Help Consumers 'Get Well and Stay Well'", New York: Jun. 2, 1999. p. 1.*
PR Newswire, "WellMed Promotes Women's Health Awareness With Launch of Six Online Health Management Tools", New York: Oct. 2, 2000. p. 1.*

* cited by examiner

*Primary Examiner*—Luke Gilligan
*Assistant Examiner*—Robert Sorey
(74) *Attorney, Agent, or Firm*—Rohm & Monsanto, PLC (57) ABSTRACT

A system generates one or more of a plurality of wellness programs for a user. Personal data items are entered into a computing system corresponding to a personal profile of the user. A selected one or more of the plurality of wellness programs desired by the user is identified. Selected ones of the plurality of personal data items are then extracted in response to the selected one of the plurality of wellness programs. Then a corresponding plurality of wellness program data elements in response to the selected ones of the plurality of personal data items is determined. The selected plurality of wellness program data elements are then assembled to form a customized wellness program responsive to the step of identifying a selected one of the plurality of wellness programs and the selected ones of the plurality of personal data items. The customized wellness program is recorded on media for the user.

30 Claims, 4 Drawing Sheets

PERSONALIZED AUDIO/VIDEO/TEXT WELLNESS PROGRAM

RELATIONSHIP TO OTHER APPLICATION

This application is a US national stage filing under 35 U.S.C. §371 of International Application No. PCT/US2005/011034 filed on Apr. 1, 2005 and claims the benefit under 35 U.S.C. §119(e) of U.S. Provisional Patent Application Ser. No. 60/559,253 filed Apr. 1, 2004.

BACKGROUND OF THE INVENTION

1. Field of the Invention

This invention relates generally to systems and programs for improving the well-being of an individual, and more particularly, to a computer-implemented system for generating a highly customized program that improves the psychological, spiritual, and/or physical well-being of an individual.

2. Description of the Related Art

Absent direct intervention by a professional, such as a psychologist, clergyman, trainer, nutritionist, or doctor, systems that address the psychological, spiritual, and/or physical well-being of an individual are generally not responsive to needs that are specific to the individual. Instead, such systems apply generalized concepts that may be specific to the system to all who seek to obtain the benefits that the particular system purports to provide. Thus, for example, conventional self-help, or motivational, programs set forth overall goals to be achieved and a general methodology for achieving same, but generally leave it up to the individual to apply the principles of the program to his or her specific requirements. A self-help program that can be obtained commercially on cassette, DVD, or CD media will not have provision for receiving data specific to a user, or a facility for customizing the program to the needs of the particular user.

There are myriad reasons why individuals will oftentimes seek "canned" help and decline to seek professional assistance, not the least of which are cost and denial of the severity of the underlying problem. Accordingly, there is a need for a system that can formulate wellness programs that are configured to take into consideration characteristics that are specific to the individual, while preserving privacy, i.e., without requiring the user to discuss personal issues with another person.

It is, therefore, an object of this invention to provide a system for formulating a wellness program that takes personal information into consideration in the formulation of the wellness program, at less cost than would be the case if professional intervention were to be used.

It is another object of this invention to provide a system for receiving multiple items of personal information and formulating a self-improvement program in response thereto.

It is also an object of this invention to provide a customized program product for a particular user.

It is a further object of this invention to provide a relaxation data product that contains material specifically relaxing to a particular individual.

It is additionally an object of this invention to provide a system that facilitates a human user to construct a custom psychological wellness product.

It is yet a further object of this invention to provide a system that facilitates a human user to construct a custom physical wellness product.

It is also another object of this invention to provide a system that facilitates a human user to construct a custom spiritual wellness product.

It is yet an additional object of this invention to provide a system that records a user's information on a recurring basis whereby changes in the user's wellness can be tracked.

SUMMARY OF THE INVENTION

The foregoing and other objects are achieved by this invention which provides a system for generating one of a plurality of wellness programs for a user. In accordance with a first aspect of the invention, the system includes, without limitation, the steps of:

entering a plurality of personal data items into a computing system corresponding to a personal profile of the user;

identifying a selected one of the plurality of wellness programs desired by the user;

extracting selected ones of the plurality of personal data items in response to the selected one of the plurality of wellness programs;

selecting a plurality of wellness program data elements in response to the selected ones of the plurality of personal data items;

assembling the selected plurality of wellness program data elements to form a customized wellness program responsive to the step of identifying a selected one of the plurality of wellness programs and the selected ones of the plurality of personal data items; and recording the customized wellness program on media.

In one embodiment of the invention, there is provided the further step of selecting one of a plurality of narrator voices to be used in the customized wellness program.

Prior to performing the step of entering a plurality of personal data items into a computing system there is provided the step of filling out a personal profile of the user. Such a profile may include medical and lifestyle data. In addition, the profile may include birth date information and a child number (i.e., second of four children). The resulting customized wellness program can be presented to the user as a printed item, but preferably should be in the form of a CD or DVD that include picture, video, audio, and text data. The plurality of wellness program data elements for inclusion in the customized wellness program may include an audio file, which may be a spoken presentation, background music, and audio effects. Additionally, such data elements may include a video file that includes a spoken presentation, visual background effects, and an illustrative presentation of an aspect of the customized wellness program, such as background information about the program, its duration, etc. In a further embodiment, the step of selecting a plurality of wellness program data elements includes the step of selecting workout video data elements responsive to the medical data and to the lifestyle data. In yet another embodiment of the invention, the step of selecting a plurality of wellness program data elements includes the step of selecting Chinese calendar data elements responsive to the birth date data about the user. In addition, there may be included the step of selecting Enneagram Personality data elements and/or Arevadic Body type data elements responsive to the birth date data about the user.

In a customized relaxation embodiment of the invention, there are further provided the steps of:

user listening to a plurality of available music soundtracks;

user selecting one of the plurality of available music soundtracks in response to the user's perceived relaxation response;

user listening to a plurality of available background sound effects schemes; and user selecting one of the plurality of available background sound effects schemes in response to the user's perceived enjoyment response.

In one embodiment of this customized relaxation program there are further provided the steps of:
   user listening to a plurality of available narrator voices;
   user selecting one of the plurality of available narrator voices;
   user reviewing a menu of positive affirmations;
   user selecting a positive affirmation for inclusion in the customized wellness program.

In one embodiment of the customized relaxation program, the step of user reviewing a menu of positive affirmations includes the step of reviewing a menu of topics of positive affirmations, the topics corresponding to self esteem, self confidence, stress management, self control, etc.

In accordance with a further system aspect of the invention, there is provided a system for generating a program for a client, the system having the steps of:
   filling out a questionnaire containing inquiries regarding a plurality of physical and lifestyle aspects of the client;
   obtaining a plurality of physical measurements of the client;
   obtaining a plurality of biochemical characteristics of the client;
   entering into a computing system a first data element that is responsive to responses in the questionnaire;
   entering into the computing system a second data element that is responsive to the client's physical measurements;
   entering into the computing system a third data element that is responsive to the client's biochemical measurements;
   entering into the computing system a fourth data element that is responsive to the client's psychological measurements;
   calculating a wellness quotient of the client that is responsive to the first, second, third, and fourth data elements, the wellness quotient being representative of an overall wellness condition of the client;
   selecting an item of output information from a plurality of items of information in response to the wellness quotient; and
   recording output data on media that is responsive to the selected output information.

In one embodiment of this further system aspect, the step of filling out a questionnaire includes the steps of responding to inquiries relating to the client's physical characteristics, to produce a physical questionnaire data element; responding to inquiries relating to the client's biochemical characteristics, to produce a biochemical questionnaire data element; and responding to inquiries relating to the client's psychological characteristics, to produce a psychological questionnaire data element. Physical questionnaire scoring produces a physical questionnaire score value that is responsive to the physical questionnaire data element. Biochemical questionnaire scoring produces a biochemical questionnaire score value that is responsive to the biochemical questionnaire data element. Similarly, psychological questionnaire scoring produces a psychological questionnaire score value that is responsive to the psychological questionnaire data element. In a similar manner, physical measurement scoring produces a physical measurement score value that is responsive to the second data element, biochemical measurement scoring produces a biochemical measurement score value that is responsive to the third data element, and psychological measurement scoring produces a psychological measurement score that is value responsive to the fourth data element.

In a further embodiment, the physical questionnaire score value, the biochemical questionnaire score value, the psychological questionnaire score value, the physical measurement score value, the biochemical measurement score value, and the psychological measurement score value are subjected to adjustment in response to a predetermined multiplier value.

There are provided in some embodiments of the invention the further steps of producing a physical score that is responsive to a predetermined physical score combination of the physical questionnaire score value and the physical measurement score value; producing a biochemical score that is responsive to a predetermined biochemical score combination of the biochemical questionnaire score value and the biochemical measurement score value; and producing a psychological score that is responsive to a predetermined psychological score combination of the psychological questionnaire score value and the psychological measurement score value, In the step of producing a physical score, the predetermined physical score combination ("$Ph_{hs}$") of the physical questionnaire score value ("$P_{hqsv}$") and the physical measurement score value ("$P_{hmsv}$") corresponds to the relationship:

$$P_{hs}=0.25\ P_{hqsv}+0.75\ P_{hmsv}.$$

In the step of producing a biochemical score, the predetermined biochemical score combination ("$B_s$") of the biochemical questionnaire score value ("$B_{qsv}$") and the biochemical measurement score value ("$B_{msv}$") corresponds to the relationship:

$$B_s=0.25\ B_{qsv}+0.75\ B_{msv}.$$

In the step of producing a psychological score, the predetermined psychological score combination ("$P_{ss}$") of the psychological questionnaire score value ("$P_{sqsv}$") and the psychological measurement score value ("$P_{smsv}$") corresponds to the relationship:

$$P_{ss}=0.50\ P_{sqsv}+0.50\ P_{smsv}.$$

The step of calculating a wellness quotient includes the further step of combining the physical score ("$P_{hs}$"), the biochemical score ("$B_s$"), and the psychological score ("$P_{ss}$") in accordance with a predetermined wellness quotient ("$W_q$") combination. However, in some embodiments, prior to performing the step of combining the physical score ("$P_{hs}$"), the biochemical score ("$B_s$"), and the psychological score ("$P_{ss}$") in accordance with a predetermined wellness quotient ("$W_q$") combination, there is provided the further step of transforming the physical score ("$P_{hs}$"), the biochemical score ("$B_s$"), and the psychological score ("$P_{ss}$") to produce respective ones of a transformed physical score ("$P_{ht}$"), a transformed biochemical score ("$B_t$"), and a transformed psychological score ("$P_{st}$"). The step of transforming the physical score ("$P_{hs}$"), the biochemical score ("$B_s$"), and the psychological score ("$P_{ss}$") is performed in accordance with the relationships:

$$P_{ht}=450/P_{hs};$$

$$B_t=450/B_s;\ \text{and}$$

$$P_{st}=450/P_{ss}.$$

The step of combining the physical score ("$P_{hs}$"), the biochemical score ("$P_{hs}$"), and the psychological score ("$P_{ss}$") to produce the wellness quotient ("$W_q$") is performed in accordance with the relationship:

$$W_q=(P_{ht})^{0.4}(B_t)^{0.4}(P_{st})^{0.2}.$$

In accordance with a further embodiment of the invention, there is provided in the step of selecting an item of output information the step of selecting at least one audio segment from a plurality of audio segments in response to the wellness quotient. The output information there is provided the step of selecting at least one text paragraph from a plurality of text paragraphs in response to the wellness quotient. In the step of entering into a computing system a first data element there is provided the step of entering into the computing system lifestyle data about the client. In addition, such information may include the entering into the computing system heart beat rate, and blood pressure data about the client, height, and weight data about the client.

In the step of calculating a wellness quotient of the client that is responsive to the first, second, and third data elements, there is included in some embodiments the step of assigning a weighting factor to each of the first, second, and third data elements. The weighting factors assigned to each of the first, second, and third data elements need not be equal.

One of the items that may be selected in response to the calculated wellness quotient is an item of physical exercise.

In the practice of the invention, there are provided in the course of rescheduled visits by the client the further steps of waiting a predetermined period of time, which may be approximately five weeks and second filling out a questionnaire containing inquiries regarding a plurality of physical and lifestyle aspects of the client. In addition, each subsequent visit may entail obtaining a plurality of new physical measurements of the client as well as obtaining new biochemical characteristics of the client. A new first data element that is responsive to responses to the questionnaire is entered into the computer, as well as a new second data element that is responsive to the client's physical measurements and a new third data element that is responsive to the client's biochemical characteristics. Then, a new wellness quotient of the client that is responsive to the new first, new second, and new third data elements is calculated, and an item of output information from a plurality of items of information in response to the new wellness quotient is selected. A new output data is then recorded on media, the new output data being responsive to the selected output information.

In addition to the foregoing, the wellness quotient and the new wellness quotient are compared. An item of output information from a plurality of items of information is then selected in response to the comparison of the wellness quotient and the new wellness quotient.

In accordance with a further system aspect of the invention, there is provided a system for determining and improving the wellness of a human client. The further system aspect is characterized by the steps of:

entering a plurality of personal data items into a computing system corresponding to a personal profile of the user;

identifying a wellness goal of the human client in response to the personal data items entered in the computing system;

identifying physical personal data items of the personal data items entered in the computing system that are responsive to the physical condition of the human client;

identifying biochemical personal data items of the personal data items entered in the computing system that are responsive to the biochemical condition of the human client;

identifying psychological personal data items of the personal data items entered in the computing system that are responsive to the psychological condition of the human client;

computing a physical wellness value in the computing system, the physical wellness value being responsive to the identified physical personal data items;

computing a biochemical wellness value in the computing system, the biochemical wellness value being responsive to the identified biochemical personal data items;

computing a psychological wellness value in the computing system, the psychological wellness value being responsive to the identified psychological personal data items;

computing a wellness quotient in the computing system that is responsive to the physical wellness value, the biochemical wellness value; and the psychological wellness value;

selecting a plurality of wellness program data elements in response to the selected ones of the plurality of personal data items;

assembling the selected plurality of wellness program data elements to form a customized wellness program that is responsive to the step of identifying a wellness goal of the human client and the wellness quotient; and recording the customized wellness program on media for the human client.

In accordance with this further system aspect of the invention, personal data items in the step of entering a plurality of personal data items are derived from responses to a questionnaire containing queries concerning the human client, from physical measurements of the body of the human client, and from biochemical measurements of the body of the human client. The biochemical measurements correspond, for example, to a measurement of the heart rate of the human client, the blood pressure of the human client, and the time required for a recovery of a biochemical parameter following a predetermined stimulation, such as a stressful stimulation. Thus, some of the personal data items are derived from measured responses of the human client to stress. As previously noted, the computation of a wellness quotient in the computing system is responsive to the personal profile of the user and the biochemical wellness value.

In a practicable application of the present invention, the computing system includes a remote computing server as well as a local computing substation. The entering of personal data items into the computing system is performed at the local computing substation. Also in this embodiment, the computing of a wellness quotient is performed at the remote computing server.

In accordance with a still further system aspect of the invention there is provided a system for determining and improving the wellness of a human client, the system having the steps of:

entering a plurality of personal data items into a computing system corresponding to a personal profile of the user;

identifying a wellness goal of the human client in response to the personal data items entered in the computing system;

identifying biochemical personal data items of the personal data items entered in the computing system that are responsive to the biochemical condition of the human client;

computing a wellness quotient in the computing system that is responsive to the personal profile of the user and the biochemical wellness value; and forming a customized wellness program that is responsive to the step of identifying a wellness goal of the human client and the computed wellness quotient.

In one embodiment of this further system aspect, the step of identifying a wellness goal of the human client is explicitly specified by the human client. Certain items of personal data are responsive to the physical condition of the human client. A physical wellness value is calculated in the computing system, the physical wellness value being responsive to the identified physical personal data items. There is provided in some embodiments, an item of physical exercise equipment in response to the physical wellness value.

In other embodiments, there is provided the further step of identifying psychological personal data items entered in the computing system that are responsive to the psychological condition of the human client. A psychological wellness value is calculated in the computing system in response to the identified psychological personal data items. In addition, a biochemical wellness value is calculated in the computing system, the biochemical wellness value being responsive to the identified biochemical personal data items. The customized wellness program, which is responsive to physical, biochemical, and psychological characteristics of the client is recorded on media and presented to the human client.

Prior to performing the step of recording the customized wellness program on media there is provided the step of selecting a plurality of wellness program data elements in response to the selected ones of the plurality of personal data items. This includes the further step of selecting a picture file and an audio file for inclusion in the customized wellness program. The audio file includes a file of a spoken presentation, background music, or special audio effects. Similarly, in certain embodiments a video file is selected for inclusion in the customized wellness program.

With respect to repeat applications of the present system for the benefit of the client, there is provided a waiting period that, in certain embodiments, should be approximately five weeks. A plurality of new personal data items are entered corresponding to a personal profile of the client/user, and a new wellness quotient is computed in the computing system in responsive to the new personal data items. A customized revised wellness program is then formulated that is responsive to the computed new wellness quotient.

In accordance with an apparatus aspect of the invention, there is provided a computerized arrangement for determining the wellness of a human client and formulating a wellness improvement program specific to the human client. In accordance with the invention, there is provided a data collection arrangement for collecting personal data that is responsive to the human client. A client computer system having a data input receives the personal data. Additionally, a web network is coupled to the client computer system, and a web-based server that is coupled to the web network receives from the web network client data transmitted by the client computer system to the web network. The web-based server computes a wellness quotient for the human client from the client data transmitted by the client computer system to the web network, and transmits wellness quotient data to the client computer system via the web network.

In one embodiment, a media recorder coupled to the client computer system records the wellness program specific to the human client in response to the wellness quotient data. Data collection arrangements are provided for collecting biochemical data, psychological data from the human client, and physical data from the human client.

The computerized arrangement is provided with a first memory region for storing elements of a wellness program and a second memory region for storing an application for computing the wellness quotient.

In accordance with media product aspect of the invention, there is provided a media product of the type having a plurality of data storage locations in a storage medium. A personal data storage region stores personal data items that are responsive to personal information of a client. Additionally, a wellness data storage region stores data corresponding to a wellness program customized for the client in response to the personal information of the client.

The media product can, in various embodiments, be a CD, a tape, printed material, or a DVD. The data corresponding to the wellness program is, in some embodiments, a customized relaxation program. In other embodiments, it is a personalized guided visualization program, and may include a multimedia presentation. The data corresponding to the wellness program is responsive to a pre-computed wellness quotient, as previously described herein, or a plurality of wellness quotients, including the differences between the plurality of pre-computed wellness quotients. In such an application of the invention, the plurality of pre-computed wellness quotients are each responsive to corresponding personal data collected at respective points in time, illustratively approximately five weeks.

The wellness data storage region contains a text file that is selected in response to the personal information of the client and the pre-computed wellness quotient. It may also contain an audio file that is responsive to the personal information of the client and the pre-computed wellness quotient, or a video file that is responsive to the personal information of the client and the pre-computed wellness quotient. Similarly, the file may include a graphical file, that was selected in response to the personal information of the client and the pre-computed wellness quotient.

In some embodiments of this media product aspect of the invention, the wellness data storage region contains exercise data responsive to a workout program determined in response to the personal information of the client and the pre-computed wellness quotient. Such workout programs include, for example, exercise data corresponds to a specification of strength-building exercises, flexibility-enhancing exercises, and cardiovascular fitness enhancing exercises. Nutrition information selected in response to the personal information of the client and the pre-computed wellness quotient is also included. The nutritional data corresponds to a specification of nutritional supplementation, and may include a specification of meals.

In addition to the foregoing, the wellness data storage region contains wellness journal data that is responsive to an inspirational program determined in response to the personal information of the client and the pre-computed wellness quotient.

In accordance with a further media product aspect of the invention, there is provided a media product formed by a process having the steps of:

entering a plurality of personal data items into a computing system corresponding to a personal profile of a user;

computing a wellness quotient that is responsive to the plurality of personal data items;

identifying a selected one of the plurality of wellness programs desired by the user;

extracting selected ones of the plurality of personal data items in response to the selected one of the plurality of wellness programs;

selecting a plurality of wellness program data elements in response to the selected ones of the plurality of personal data items;

assembling the selected plurality of wellness program data elements to form a customized wellness program that is responsive to the step of identifying a selected one of the plurality of wellness programs, the computed wellness quotient, and the selected ones of the plurality of personal data items; and recording the customized wellness program on a media substrate to form the media product.

In one embodiment of this further media product aspect of the invention, the media substrate is a CD.

The step of computing a wellness quotient is performed at a remote server, whereas the step of recording the customized wellness program on a media substrate is performed at a local computer station. The step of entering a plurality of personal data items also is performed at a local computer station. The plurality of personal data items correspond to physical, biochemical, and psychological aspects of the personal profile of the user.

BRIEF DESCRIPTION OF THE DRAWINGS

Comprehension of the invention is facilitated by reading the following detailed description, in conjunction with the annexed drawing, in which.

DETAILED DESCRIPTION

Figure 1:
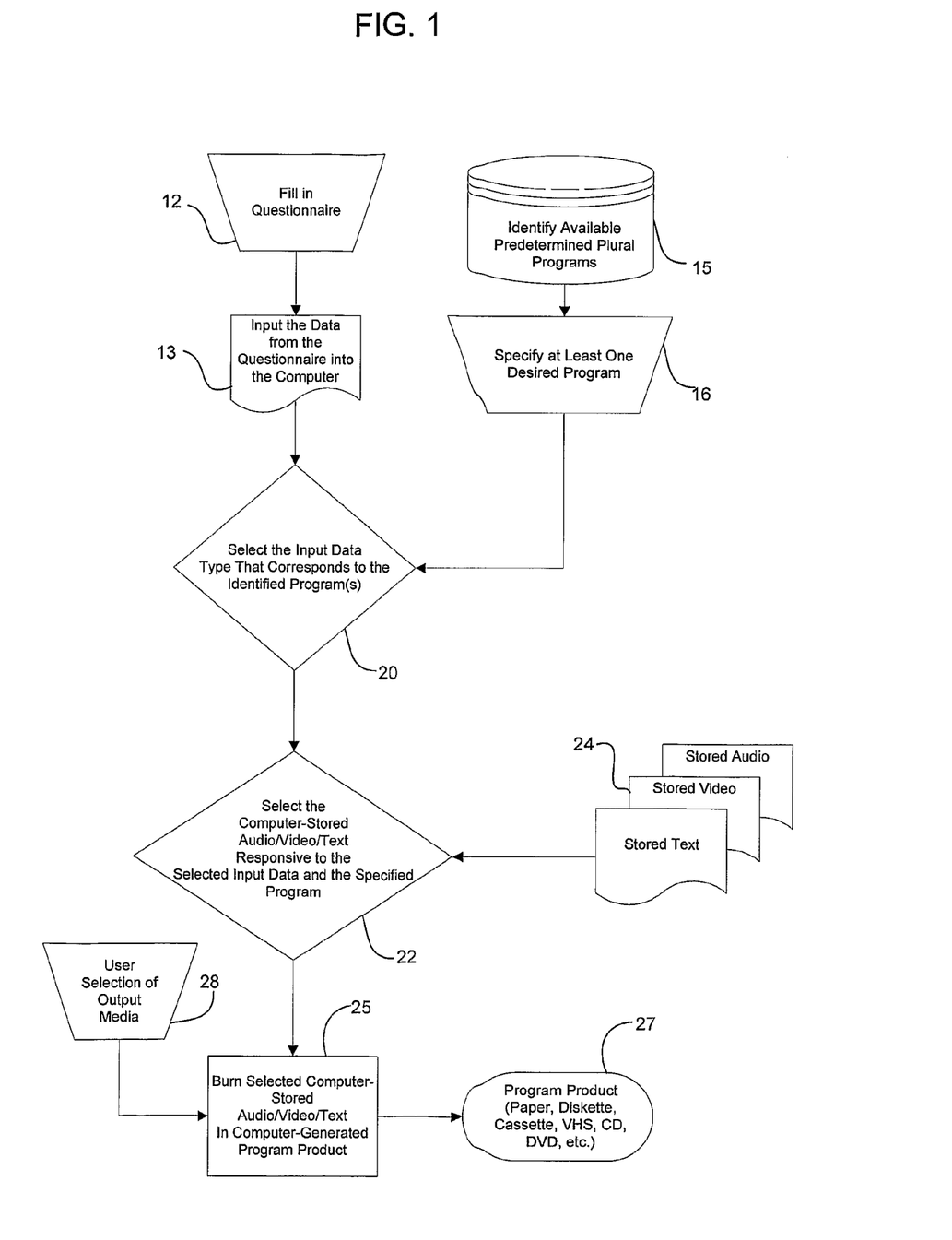
FIG. 1 is a simplified block and line representation of a general aspect of the invention.

FIG. 1 is a simplified block and line representation of a general aspect of the invention. As shown in this figure, a user (not shown) fills in a questionnaire at function block 12 from which is produced input data that is transmitted to a computer at function block 13. In a specific illustrative embodiment of the invention, the information is stored in a user or subscriber account (not shown) whereby subsequent changes in the user's information can be tracked to reveal wellness trends. A plurality of available growth characteristics, or wellness programs, such as Financial Independence, Self Esteem, Spiritual Growth, Physical Wellness, Weight Loss, Cardio-Vascular Health, Substance Abuse, Family Relationships, etc. are displayed to the user at function block 15, and at least one such program is selected at function block 16.

A determination is made at function block 20 to select items of input data that are of a type that corresponds to the programs selected at function block 16. Thus, for example, data corresponding to height and weight would be selected in response to the selection of a weight loss or cardio-vascular program at function block 16.

In addition to the selection of the appropriately corresponding type of input data, stored material at function block 24, which maybe audio, video, or text data, is selected at function block 22 in response to the selected program (at function block 16) and the input data (at function block 20). The selected audio/video/text data then is recorded onto media at function block 25 to create a program product 27 that may consist of any combination of paper-printed material, a computer diskette, an audio cassette or CD, a VHS tape, a CD-ROM, and/or a DVD-ROM. In some embodiments, the user can select the desired output media for the program, such as at function block 28.

Figure 2:
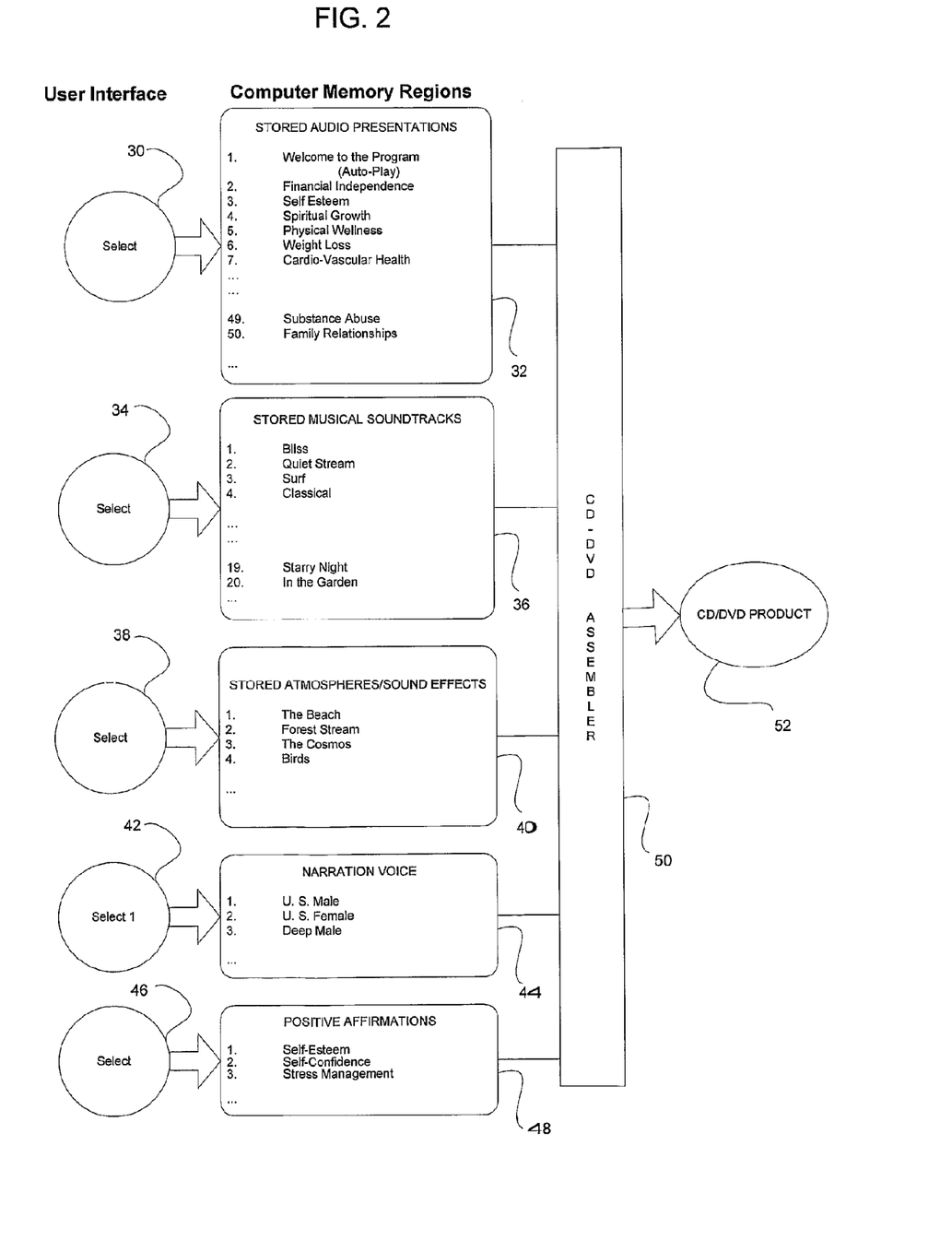
FIG. 2 is a simplified block and line representation of a computer media product formed in accordance with the principles of the invention.

FIG. 2 is a simplified block and line representation of a computer media product formed in accordance with the principles of the invention. As shown in this figure, A user (not shown) gains limited access to certain computer memory regions via a user interface. The user then is permitted to make certain selections. In the specific illustrative embodiment of the invention depicted in this figure, the user makes a selection at function block 30 of certain audio presentations stored in the memory region 32. These audio presentations include, for example:

1. Welcome to the Program (Auto-Play)
2. Financial Independence
3. Self Esteem
4. Spiritual Growth
5. Physical Wellness
6. Weight Loss
7. Cardio-Vascular Health
. . .
. . .
49. Substance Abuse
50. Family Relationships
. . .

At function block 34, the user selects from predetermined musical soundtracks stored in memory region 36, which may include, for example:

1. Bliss
2. Quiet Stream
3. Surf
4. Classical
. . .
. . .
19. Starry Night
20. In the Garden At function block 38, the user selects from predetermined atmospheres/sound effects stored in memory region 40, which may include, for example:

1. The Beach
2. Forest Stream
3. The Cosmos
4. Birds
. . .

At function block 42, the user selects from predetermined narration voices stored in memory region 44, which may include, for example:

1. U.S. Male
2. U.S. Female
3. Deep Male
. . .

At function block 46, the user selects from predetermined positive affirmations stored in memory region 48, which may include, for example:

1. Self Esteem
2. Self Confidence
3. Stress Management
. . .

In this specific illustrative embodiment of the invention, the selected elements of data stored in the respective computer memory regions is assembled into an appropriate program product in CD/DVD assembler 50. A CD/DVD program product is produced at function block 52.

Figure 3:
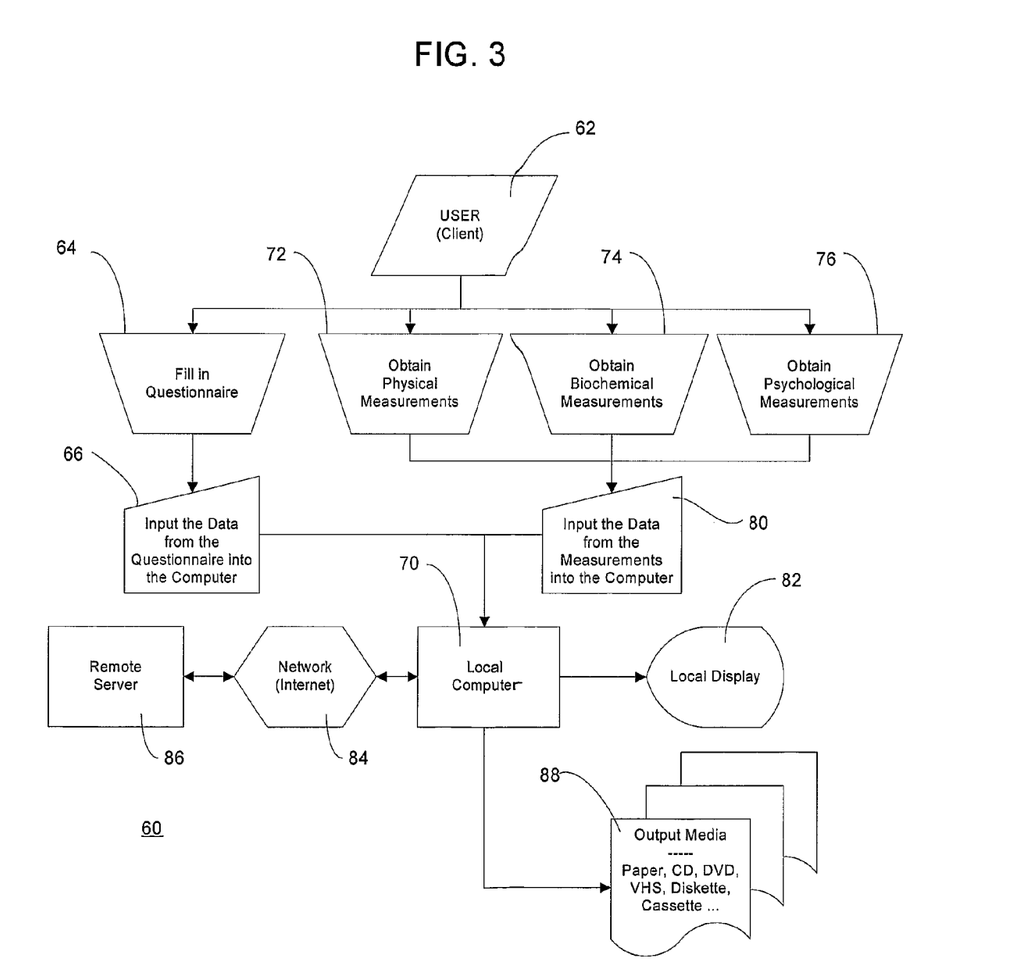
FIG. 3 is a simplified function block representation of a specific illustrative embodiment of the invention in the form of a system for formulating a customized wellness program for a client.

FIG. 3 is a simplified function block representation of a specific illustrative embodiment of the invention in the form of a system for formulating a customized wellness program for a client. As shown in this figure, a wellness system 60 receives from a user 62, who may be the client, responses to a questionnaire at function block 64. This information is input as raw data into a local computer 70 via an input arrangement 66, which may be a conventional keyboard or other input device. There is additionally obtained from user 62 physical measurements at function block 72, biochemical measurements at function block 74, and psychological measurements at function block 76. All of such raw data is input via input device 80 to local computer 70. In certain embodiments of the invention, data from the questionnaire and the data from the various measurements are entered via a single, shared input apparatus (e.g., a single keyboard).

Local computer 70 may be of a conventional type having a display 82 for facilitating an interface with user 62. In certain embodiments, the local computed is connected via a network 84, which may be the Internet, to a remote server 86. The computation and data storage functions that will be described herein may be shared between the local computer and the remote server. However, in other embodiments, all computational functions are performed in the local computer. Upon completion of the computations, as herein described, a customized wellness product is issued for the client in the form of output media 88. As previously noted, the output media may consist of any combination of paper-printed material, a computer diskette, an audio cassette or CD, a VHS tape, a CD-ROM, and/or a DVD-ROM (not specifically shown).

Figure 4:
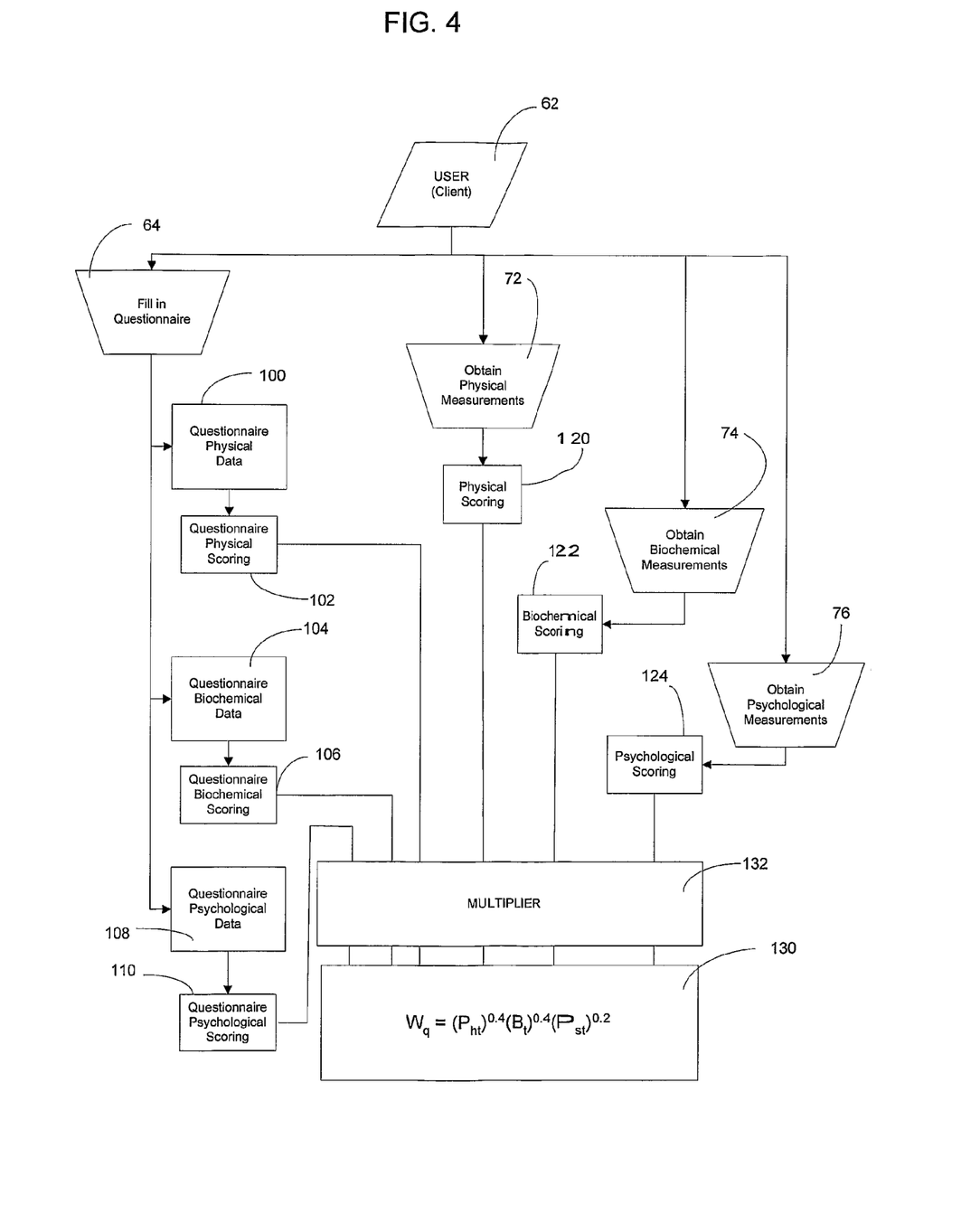
FIG. 4 is a simplified block and line representation of a method of computing a wellness quotient in accordance with the invention.

FIG. 4 is a simplified block and line representation of a method of computing a wellness quotient in accordance with the invention. Functional elements that previously have been described are similarly designated. As previously described in connection with FIG. 3, and as shown in FIG. 4, user 62 fills in a questionnaire at function block 64, and provides physical measurements at function block 72, biochemical measurements at function block 74, and psychological measurements at function block 76. The questionnaire (not shown), contains questions relating to physical characteristics of the user, as well as biochemical and psychological characteristics. The responses to these queries constitute questionnaire physical data at function block 100, questionnaire biochemical data at function block 104, and questionnaire psychological data at function block 108.

Each of these elements of questionnaire data is subsequently scored, the questionnaire physical data being scored at function block 102, the questionnaire biochemical data being scored at function block 106, and the questionnaire psychological data being scored at function block 110. In this specific illustrative embodiment of the invention, scoring of the raw data is scaled to range from 0 to 10, where 0 is the best possible score and 10 is the worst possible score. In a practical embodiment of the invention, the scaled scores correspond to the following levels of performance:

| Scores | Corresponding Performance |
| --- | --- |
| 0.0 to 2.99 | unexpectedly high performance |
| 3.0 to 4.49 | excellent wellness scores |
| 4.5 to 5.99 | mild negative stress |
| 6.0 to 7.49 | moderate negative stress |
| 7.5 to 8.99 | severe negative stress |
| 9.0 to 10.0 | beyond negative stress |

In addition to the three questionnaire scores, three further corresponding scores are obtained from measurements. The physical measurements are scored at function block 120, the biochemical measurements are scored at function block 122, and the psychological scoring is performed at function block 124. There are therefore six scores delivered to wellness quotient computation at function block 130. In certain embodiments of the invention, the six scores are adjusted by a multiplier arrangement 132.

In the production of the physical score, the predetermined physical score combination ("$P_{hs}$") of the physical questionnaire score value ("$P_{hqsv}$") and the physical measurement score value ("$P_{hmsv}$") correspond to the relationship:

$$P_{hs} = 0.25\, P_{hqsv} + 0.75\, P_{hmsv}.$$

With respect to the biochemical score, the predetermined biochemical score combination ("$B_s$") of the biochemical questionnaire score value ("$B_{qsv}$") and the biochemical measurement score value ("$B_{msv}$") correspond to the relationship:

$$B_s = 0.25\, B_{qsv} + 0.75\, B_{msv}.$$

Consequently, the predetermined psychological score combination ("$P_{ss}$") of the psychological questionnaire score value ("$P_{sqsv}$") and the psychological measurement score value ("$P_{smsv}$") correspond to the relationship:

$$P_{ss} = 0.50\, P_{sqsv} + 0.50\, P_{smsv}.$$

The calculation of the Wellness Quotient at function block 130 combines the physical score ("$P_{hs}$"), the biochemical score ("$B_s$"), and the psychological score ("$P_{ss}$") in accordance with a predetermined wellness quotient ("$W_q$") combination. More specifically, in an illustrative embodiment of the invention, the combining of the physical score ("$P_{hs}$"), the biochemical score ("$B_s$"), and the psychological score ("$P_{ss}$") in accordance with a predetermined wellness quotient ("$W_q$") combination, the physical score ("$P_{hs}$"), the biochemical score ("$B_s$"), and the psychological score ("$P_{ss}$") are transformed to produce respective ones of a transformed physical score ("$P_{ht}$"), a transformed biochemical score ("$B_t$"), and a transformed psychological score ("Pst"). The transformation of the physical score ("$P_{hs}$"), the biochemical score ("$B_s$"), and the psychological score ("$P_{ss}$") is performed in accordance with the relationships:

$$P_{ht} = 450/P_{hs};$$

$$B_t = 450/B_s; \text{ and}$$

$$P_t = 450/P_{ss}.$$

Finally, in this specific illustrative embodiment, the physical score ("$P_{hs}$"), the biochemical score ("$P_{hs}$"), and the psychological score ("$P_{ss}$") are combined to produce the wellness quotient ("$W_q$") in accordance with the relationship:

$$W_q = (P_{ht})^{0.4}(B_t)^{0.4}(P_{st})^{0.2}$$

Although the invention has been described in terms of specific embodiments and applications, persons skilled in the art may, in light of this teaching, generate additional embodiments without exceeding the scope or departing from the spirit of the invention claimed herein. Accordingly, it is to be understood that the drawing and description in this disclosure are proffered to facilitate comprehension of the invention, and should not be construed to limit the scope thereof.

What is claimed is:

1. A method of generating a personalized wellness program for a human client, the method comprising the steps of:

entering into a computer system, by a user, responses to a questionnaire containing inquiries regarding a plurality of physical and lifestyle aspects of the human client;

wherein the responses to the inquiries relate to the human client's physical characteristics, biochemical characteristics, and psychological characteristics;

entering into the computer, by the user, a plurality of the human client's physical measurements, biochemical measurements, and psychological measurements;

calculating, by the computer system, a transformed physical score ("Pht") based on the entered questionnaire responses relating to the human client's physical characteristics and the human client's entered physical measurements, a transformed biochemical score ("Bt") based on the entered questionnaire responses relating to the human client's biochemical characteristics and the human client's entered biochemical measurements, and a transformed psychological score ("Pst") based on the entered questionnaire responses relating to the human client's psychological characteristics and the human client's entered psychological measurements;

calculating, by the computer system, a wellness quotient ("Wq") of the human client, the wellness quotient being representative of an overall wellness condition of the human client, wherein the wellness quotient ("Wq") is calculated in accordance with the relationship:

$$Wq=(Pht)^{0.4}(Bt)^{0.4}(Pst)^{0.2};$$

selecting and outputting, by the computer system, an item of output information from a plurality of items of information based on the calculated to the wellness quotient; and recording, by the computer system, the item of output information on media responsive to the selecting of output information.

2. The method of claim 1, wherein the responses to the questionnaire include:
  responses to inquiries relating to the human client's physical characteristics, to produce a physical questionnaire data element;
  responses to inquiries relating to the human client's biochemical characteristics, to produce a biochemical questionnaire data element; and
  responses to inquiries relating to the human client's psychological characteristics, to produce a psychological questionnaire data element.

3. The method of claim 2, wherein the computer system further performs the steps of:
  physical questionnaire scoring for producing a physical questionnaire score value responsive to the physical questionnaire data element;
  biochemical questionnaire scoring for producing a biochemical questionnaire score value responsive to the biochemical questionnaire data element; and
  psychological questionnaire scoring for producing a psychological questionnaire score value responsive to the psychological questionnaire data element.

4. The method of claim 3, wherein the computer system further performs the steps of:
  physical measurement scoring for producing a physical measurement score value responsive to the second data element;
  biochemical measurement scoring for producing a biochemical measurement score value responsive to the third data element; and
  psychological measurement scoring for producing a psychological measurement score value responsive to the fourth data element.

5. The method of claim 4, wherein the computer system further performs the steps of:
  producing a physical score ("Phs") responsive to a predetermined combination of the physical questionnaire score value and the physical measurement score value;
  producing a biochemical score ("Bs") responsive to a predetermined combination of the biochemical questionnaire score value and the biochemical measurement score value; and
  producing a psychological score ("Pss") responsive to a predetermined combination of the psychological questionnaire score value and the psychological measurement score value.

6. The method of claim 5, wherein there is provided the further step of transforming the physical score ("Phs"), the biochemical score ("Bs"), and the psychological score ("Pss") to produce respective ones of a transformed physical score ("Pht"), a transformed biochemical score ("Bt"), and a transformed psychological score ("Pst").

7. The method of claim 6, wherein said step of transforming the physical score ("Phs"), the biochemical score ("Bs"), and the psychological score ("Pss") is performed in accordance with the relationships:

$$Pht=450/Phs;$$

$$Bt=450/Bs; \text{ and}$$

$$Pst=450/Pss.$$

8. The method of claim 7, wherein the physical score ("Phs"), the biochemical score ("Bs"), and the psychological score ("Pss") are combined to produce the wellness quotient ("Wq").

9. The method of claim 5, wherein in said step of producing a physical score, the predetermined physical score combination ("Phs") of the physical questionnaire score value ("Phqsv") and the physical measurement score value ("Phmsv") corresponds to the relationship:

$$Phs=0.25 \, Phqsv+0.75 \, Phmsv.$$

10. The method of claim 5, wherein in said step of producing a biochemical score, the predetermined biochemical score combination ("Bs") of the biochemical questionnaire score value ("Bqsv") and the biochemical measurement score value ("Bmsv") corresponds to the relationship:

$$Bs=0.25 \, Bqsv+0.75 \, Bmsv.$$

11. The method of claim 5, wherein in said step of producing a psychological score, the predetermined psychological score combination ("Pss") of the psychological questionnaire score value ("Psqsv") and the psychological measurement score value ("Psmsv") corresponds to the relationship:

$$Pss=0.50 \, Psqsv+0.50 \, Psmsv.$$

12. The method of claim 4, wherein the computer system further performs the steps of subjecting the physical questionnaire score value, the biochemical questionnaire score value, the psychological questionnaire score value, the physical measurement score value, the biochemical measurement score value, and the psychological measurement score value to adjustment in response to a predetermined multiplier value.

13. The method of claim 1, wherein there are provided the further steps of:
  waiting a predetermined period of time;
  entering into a computer system, by a user, new responses to a questionnaire containing inquiries regarding a plurality of physical and lifestyle aspects of the human client;
  wherein the new responses to the questionnaire relate to the human client's physical characteristics, biochemical characteristics, and psychological characteristics;
  entering into the computer system, by the user, a plurality of the human client's new physical measurements, biochemical measurements, and psychological measurements;
  calculating, by the computer system, a new transformed physical score ("Pht") based on the newly entered questionnaire responses relating to the human client's physical characteristics and the human client's entered physical measurements, a new transformed biochemical score ("Bt") based on the newly entered questionnaire responses relating to the human client's biochemical characteristics and the human client's entered biochemical measurements, and a new transformed psychological score ("Pst") based on the newly entered questionnaire responses relating to the human client's psychological characteristics and the human client's entered psychological measurements;

calculating, by the computer system, a new wellness quotient ("Wq") of the human client, the wellness quotient being representative of an overall wellness condition of the human client, wherein the new wellness quotient ("Wq") is calculated in accordance with the relationship:

$$Wq=(pht)^{0.4}(Bt)^{0.2};$$

selecting and outputting, by the computer system, an item of output information from a plurality of items of information based on the calculated to the wellness quotient; and recording, by the computer system, the item of output information on media responsive to the selecting of output information.

14. The method of claim 13, wherein the predetermined period of time is five weeks.

15. The method of claim 13, wherein the computer system further performs the steps of:
comparing the wellness quotient and the new wellness quotient; and
selecting and outputting an item of information from a plurality of items of information based on said step of comparing the wellness quotient and the new wellness quotient.

16. The method of claim 1, wherein in said step of selecting and outputting an item of information there is provided the step of selecting at least one audio segment from a plurality of audio segments based on the wellness quotient.

17. The method of claim 1, wherein in said step of selecting and outputting an item of information there is provided the step of selecting at least one text paragraph from a plurality of text paragraphs based on the wellness quotient.

18. The method of claim 1, wherein in said step of entering into a computing system responses to a questionnaire containing inquiries regarding a plurality of physical and lifestyle aspects of the human client includes the step of entering into the computing system lifestyle data, heart beat rate data, blood pressure data, and height and weight data about the human client.

19. The method of claim 1, wherein in said step of selecting and outputting by the computer system there is provided the step of selecting an item of physical exercise based on the calculated wellness quotient.

20. A system for determining and improving the wellness of a human client, the system comprising:
a computer system configured to receive entered responses to a questionnaire containing inquiries regarding a plurality of physical and lifestyle aspects of the human client, wherein responses to the inquiries relate to the human client's physical characteristics, biochemical characteristics, and psychological characteristics;
the computer system configured to receive the human client's entered physical measurements, biochemical measurements, and psychological measurements;
the computer system configured to calculate a transformed physical score ("Pht") based on the entered questionnaire responses relating to the human client's physical characteristics and the human client's entered physical measurements, a transformed biochemical score ("Bt") based on the entered questionnaire responses relating to the human client's biochemical characteristics and the human client's entered biochemical measurements, and a transformed psychological score ("Pst") based on the entered questionnaire responses relating to the human client's psychological characteristics and the human client's entered psychological measurements;
the computer system configured to calculate a wellness quotient ("Wq") of the human client, the wellness quotient being representative of an overall wellness condition of the human client, wherein the wellness quotient ("Wq") is calculated in accordance with the relationship:

$$Wq=(Pht)^{0.4}(Bt)^{0.4}(Pst)^{0.2};$$

the computer system configured to form a customized wellness program based on the calculated wellness quotient ("Wq") of the human client.

21. The system of claim 20, wherein the computer system is further configured to:
receive new entered responses to a questionnaire containing inquiries regarding a plurality of physical and lifestyle aspects of the human client, wherein responses to the inquiries relate to the human client's physical characteristics, biochemical characteristics, and psychological characteristics;
receive the human client's new entered physical measurements, biochemical measurements, and psychological measurements;
calculate a new transformed physical score ("Pht") based on the newly entered questionnaire responses relating to the human client's physical characteristics and the human client's entered physical measurements, a new newly transformed biochemical score ("Bt") based on the entered questionnaire responses relating to the human client's biochemical characteristics and the human client's entered biochemical measurements, and a new transformed psychological score ("Pst") based on the newly entered questionnaire responses relating to the human client's psychological characteristics and the human client's entered psychological measurements;
calculate a new wellness quotient ("Wq") of the human client, the wellness quotient being representative of an overall wellness condition of the human client, wherein the wellness quotient ("Wq") is calculated in accordance with the relationship:

$$Wq=(Pht)^{0.4}(Bt)^{0.4}(Pst)^{0.2};\text{ and}$$

forming a customized revised wellness program based on the inputted new calculated wellness quotient ("Wq") of the human client.

22. The system of claim 21 wherein the predetermined period of time is approximately five weeks.

23. The system of claim 21 wherein the computer system is further configured to form a customized revised wellness program, and to compare the wellness quotient and the new wellness quotient.

24. The system of claim 20, wherein the computer system is configured to provide an item of physical exercise equipment based on the wellness quotient ("Wq").

25. A computer program media product of the type having a plurality of data storage locations tangibly embodied on a computer readable medium, that when executed by a computing device performs the method steps comprising:
accessing personal data items stored in a personal data storage region, the personal data items being based on personal information of a human client that is based on responses to a questionnaire containing inquiries regarding a plurality of physical and lifestyle aspects of the human client, relating to the human client's physical characteristics, biochemical characteristics, and psychological characteristics, the personal data items being tangibly embodied in the personal data storage region, and having been precalculated by a computing system as a transformed physical score ("Pht") based on the entered questionnaire responses relating to the human client's physical characteristics and the human client's entered physical measurements, a transformed biochemical score ("Bt") based on the entered questionnaire responses relating to the human client's biochemical characteristics and the human client's entered biochemical measurements, and a transformed psychological score ("Pst") based on the entered questionnaire responses relating to the human client's psychological characteristics and the human client's entered psychological measurements; and accessing and presenting to the human client a pre-computed wellness program customized for the human client in response to the personal information of the human client, the wellness program being based on a pre-computed wellness quotient ("Wq") and tangibly embodied in a wellness data storage region, the wellness quotient having been pre-computed in accordance with the relationship:

$Wq=(Pht)^{0.4}(Bt)^{0.4}(Pst)^{0.2}$.

26. The computer program product of claim 25, wherein the wellness program is a customized relaxation program.

27. The computer program product of claim 26, wherein the customized relaxation program is a personalized guided visualization program.

28. The computer program product of claim 25, wherein the wellness program is a multimedia presentation.

29. The computer program product of claim 25, wherein the wellness program includes exercise data responsive to a workout program based on the personal information of the human client and the pre-computed wellness quotient.

30. The computer program product of claim 25, wherein the wellness program includes data nutritional data responsive to a nutrition program determined in response to the personal information of the human client and the pre-computed wellness quotient.

* * * * *